United States Patent [19]

Crawley et al.

[11] Patent Number: 5,397,628
[45] Date of Patent: Mar. 14, 1995

[54] LAMINATED, AIR IMPERMEABLE CELLULAR RUBBER, BODY PROTECTION MATERIAL WITH POROUS, EXPANDED POLYTETRAFLUOROETHYLENE LAYER

[75] Inventors: Jerald M. Crawley; Steven C. Newman, both of Flagstaff, Ariz.

[73] Assignee: W. L. Gore & Associates, Inc., Newark, Del.

[21] Appl. No.: 180,393

[22] Filed: Jan. 12, 1994

Related U.S. Application Data

[63] Continuation of Ser. No. 765,650, Sep. 25, 1991, abandoned.

[51] Int. Cl.⁶ .................................................. B32B 7/00
[52] U.S. Cl. .................................. 428/246; 428/314.4; 428/316.6; 428/317.7; 428/319.3; 428/422
[58] Field of Search ............... 428/314.4, 316.6, 317.1, 428/317.7, 319.3, 246, 422

[56] References Cited

U.S. PATENT DOCUMENTS

| | | | |
|---|---|---|---|
| 4,133,927 | 1/1979 | Tomoda | 428/215 |
| 4,443,511 | 4/1984 | Worden et al. | 428/198 |
| 4,692,369 | 9/1987 | Nomi | 428/198 |
| 5,043,209 | 8/1991 | Boissé et al. | 428/233 |
| 5,102,711 | 4/1992 | Keller et al. | 428/71 |

FOREIGN PATENT DOCUMENTS

| | | |
|---|---|---|
| 803980 | 1/1969 | Canada ........................... 154/104 |
| 0397998 | 11/1990 | European Pat. Off. . |
| 59-048150 | 3/1984 | Japan . |
| 1354875 | 5/1974 | United Kingdom . |
| 2021040 | 11/1979 | United Kingdom . |

*Primary Examiner*—George F. Lesmes
*Assistant Examiner*—Christopher W. Raimund
*Attorney, Agent, or Firm*—Wayne D. House

[57] ABSTRACT

A cellular rubber body protection material having an inner layer of porous expanded PTFE. It is useful as, for example, a wet suit or orthopedic brace, offering improved wearing comfort and reducing allergenic reactions in comparison to conventional cellular rubber body protection materials.

6 Claims, 2 Drawing Sheets

LAMINATED, AIR IMPERMEABLE CELLULAR RUBBER, BODY PROTECTION MATERIAL WITH POROUS, EXPANDED POLYTETRAFLUOROETHYLENE LAYER

This application is a continuation of application Ser. No. 07/765,650 filed Sep. 25, 1991.

FIELD OF THE INVENTION

This invention relates to a laminated, air impermeable cellular rubber, body protection material useful for wet suits and orthopedic braces.

BACKGROUND OF THE INVENTION

Cellular rubber, especially neoprene, has long been used as a body protection material. It is commonly used for wet suits where its insulating ability inhibits heat loss from a human body to surrounding cooler water. Wet suits are not intended to be waterproof but rather allow a thin layer of water to exist between the cellular rubber and the body surface, the thin layer of water being warmed by the human body. Cellular rubber, particularly neoprene, is also frequently used as an orthopedic brace material useful for surrounding and supporting, for example, ankles, knees, wrists and other body portions requiring some support while still allowing some flexibility or movement.

While these conventional cellular rubber body protection materials function effectively as either thermal insulation or orthopedic support materials, they are notoriously uncomfortable if worn for any length of time. Wet suits are difficult to put on and remove because of the high friction, sticky characteristic of the cellular rubber against the skin that resists fitting the garment into place. This same characteristic resists any movement between the cellular rubber and adjacent skin and results in discomfort during body movement. The presence of a thin layer of water between the cellular rubber and skin does little to improve the lack of movement between the cellular rubber and adjacent skin. Cellular rubber orthopedic braces suffer from the same problem. Further, perspiration is trapped between the cellular rubber and the skin, causing a sticky, clammy and itchy sensation that adds to the feeling of discomfort. Cellular rubber is also known to irritate the skin of many wearers and causes allergenic reactions in some cases.

SUMMARY OF THE INVENTION

The present invention relates to a body protection material comprising a laminate of an outer layer of cellular rubber and an inner layer of porous expanded polytetrafluoroethylene (hereinafter PTFE). It has been found that a thin inner layer of porous expanded PTFE offers a substantial increase in wearing comfort of cellular rubber wet suits and orthopedic braces. Further, the PTFE layer prevents skin irritation and allergenic reactions caused by prolonged contact between skin and the cellular rubber. The inner layer of porous expanded PTFE is preferably laminated to the outer layer of cellular rubber using an adhesive such as silicone. Silicones are the preferred adhesives, however, other elastomeric adhesives such as polyurethanes, acrylics and rubber-based adhesives may also be used. The adhesive may be in the form of a thin continuous layer or alternatively in a discontinuous pattern such as a dot matrix. The adhesive may or may not occlude the pores near the surface of the porous expanded PTFE; it is only necessary that the adhesive cover the surface portion of the porous expanded PTFE that is in contact with the adjacent surface portion of the cellular rubber. When applied in a discontinuous pattern some portions of the surface portion of the porous expanded PTFE are intentionally not covered by adhesive.

Cellular rubber is herein defined as any substantially air impermeable rubber material having a bulk volume containing a significant quantity of air within pores or cells when the material exists in an air environment. This description includes closed cell cellular rubber where the individual cells are not in communication with each other, and open cell cellular rubber where the cells are in communication. To be substantially air impermeable, these open cell cellular rubber materials must have at least one surface or layer that is closed or sealed to provide substantial air impermeability. The cellular rubber contains a quantity of air significant enough to cause its density to be less than that of the same rubber in a solid, non-cellular form and has a "spongy" feel offering less resistance to compressive forces than solid rubber. Cellular neoprene is the preferred cellular rubber for use in the present invention.

U.S. Pat. Nos. 3,953,566 and 4,187,390 describe the preparation of the porous, expanded PTFE film layer from which the present invention is made. It is believed that the porosity characterics of the porous expanded PTFE film layer are not of particular importance, however, a porosity of greater than 50% is preferred. Further, it is preferred that the layer be reasonably thin, for example, less than about 0.010 inches, so as not to interfere with the flexibility of the body protection material. While particular film characteristics are described for the examples incorporated subsequently herein, these porosity characteristics are not believed to be particularly preferred.

The thin layer of porous expanded PTFE adds a high degree of lubricity to the inner surface of the body protection material. This allows for a small amount of relative movement between the material and the skin. The result is a significant increase in wearing comfort. Further, because of the increased lubricity, wet suits and orthopedic braces made of the inventive body protection material are much easier to put on and remove. The porous characteristic of the porous, expanded PTFE substantially reduces the sticky, clammy and itchy feeling of cellular rubber orthopedic braces caused by perspiration trapped between the skin and the cellular rubber. It is believed that the presence of the thin layer of porous expanded PTFE provides the body protection material with some slight capacity to absorb moisture and consequently increase comfort. Further, the presence of the thin layer of porous expanded PTFE is expected to substantially reduce the likelihood of an allergenic reaction to the body protection material because the PTFE is extremely chemically inert. The porous expanded PTFE does not interfere with the existing functional qualities of providing thermal insulation or orthopedic support.

The porous expanded PTFE may preferably have a coating of hydrophilic, liquid water impermeable, water vapor permeable polyurethane as taught by U.S. Pat. No. 4,194,041, herein incorporated by reference. The coating may be on the inner surface of the porous expanded PTFE where it is in contact with the skin of a wearer. The use of such a urethane coating prevents occlusion of the pores of the porous expanded PTFE by contamination from skin oils. The lubricity of such a coated inner layer is substantially improved over that of cellular rubber alone. The water vapor permeability of the polyurethane contributes to increased comfort of the inventive material. This embodiment is preferred for orthopedic braces that are expected to be worn for long, continuous periods of time such as twelve weeks. This embodiment is also useful for shorter periods such as about two hours that may involve high rates of perspiration producing activity, such as athletic activity.

The polyurethane coating can alternatively be placed on the side of the porous expanded PTFE inner layer adjacent to the outer cellular rubber layer where it serves as the adhesive to bond the porous expanded PTFE to the cellular rubber. A third alternative allows the use of the polyurethane coating on both sides of the layer of porous expanded PTFE for the reasons described above.

For orthopedic brace applications, an alternative embodiment incorporates a thin layer of air permeable padding between the outer substantially air impermeable cellular rubber layer and the inner porous expanded PTFE layer. The layer of air permeable padding increases the ability of the laminate to absorb perspiration. The padding must be thin enough to allow the outer layer of cellular rubber to provide an effective amount of physical support for the area to which it is applied. The layer of padding is adhered to the adjacent inner and outer layers by the use of an adhesive such as silicone which may be applied either continuously or discontinuously.

Other applications of the inventive body protection material may include its use as a stump covering for amputees. The lubricity, porosity and cushioning ability of the inventive material are expected to be of value in such an application. Similar padding applications may include shoulder pads, helmet liners, knee pads and chest pads.

Cellular rubber orthopedic braces frequently include an outer covering of a fabric laminated to the outer surface of the cellular rubber. This is done in order to increase the effective amount of support provided by the brace or to provide physical protection to the cellular rubber. The inventive body protection material may also optionally incorporate an outer layer of a supporting fabric.

DETAILED DESCRIPTION OF THE INVENTION

Figure 1:
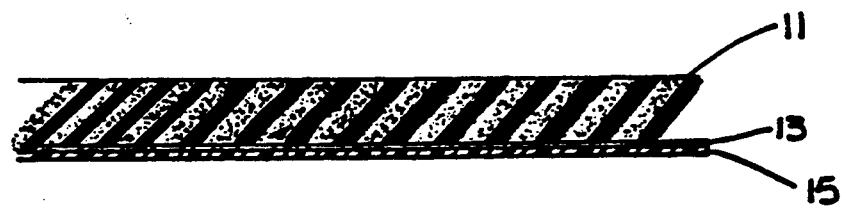
FIG. 1 describes an enlarged cross section of the body protection material of the present invention showing the inner layer of porous expanded PTFE adhered to the outer layer of cellular rubber with a continuous adhesive applied in a thin, uniform layer.

FIG. 1 shows an enlarged cross section of the body protection material of the present invention wherein the inner layer of porous expanded PTFE 15 is adhered to the outer layer of cellular rubber 11 with a continuous adhesive 13 applied over the full contact area. The adhesive is preferably a silicone or polyurethane elastomer. The adhesive need only be applied in a thin layer such as about 0.001 inch thickness.

Figure 2:
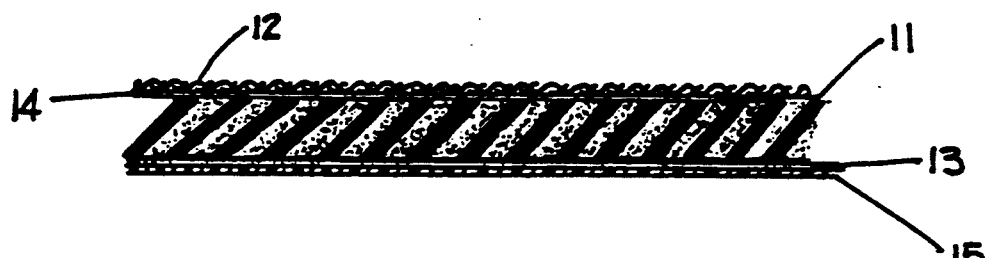
FIG. 2 describes an enlarged cross section of the body protection material of the present invention showing the inner layer of porous expanded PTFE adhered to the outer layer of cellular rubber with a continuous adhesive applied in a thin, uniform layer and further having an optional outer layer of fabric bonded to the outer surface of the layer of cellular rubber.

FIG. 2 shows an enlarged cross section of the body protection material described in FIG. 1 with an optional additional layer of supporting fabric 12 bonded to the outer surface of the layer of cellular rubber 11 using an additional layer of adhesive 14. The same adhesives may be used to adhere the fabric as are used to adhere the layer of porous expanded PTFE. The optional supporting fabric layer 12 is particularly useful in orthopedic braces where it can provide additional support.

Figure 3:
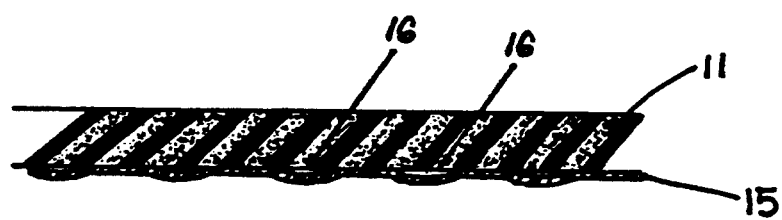
FIG. 3 describes an enlarged cross section of the body protection material of the present invention showing the inner layer of porous expanded PTFE adhered to the outer layer of cellular rubber with a discontinuous adhesive in a dot matrix pattern.

FIG. 3 shows an enlarged cross section of the inventive material wherein the adhesive 16 is applied in a discontinuous dot matrix pattern between the adjacent layers 11 and 15. The same types of adhesives are appropriate for discontinuous applications as were described for continuous applications. When the adhesive is applied in a discontinuous fashion, it is apparent that enough area of the adjacent layers must be covered by adhesive in order to provide a suitable bond between the adjacent layers. For discontinuously applied adhesives, the amount of area covered by these adhesives will need to be determined experimentally.

Figure 4:
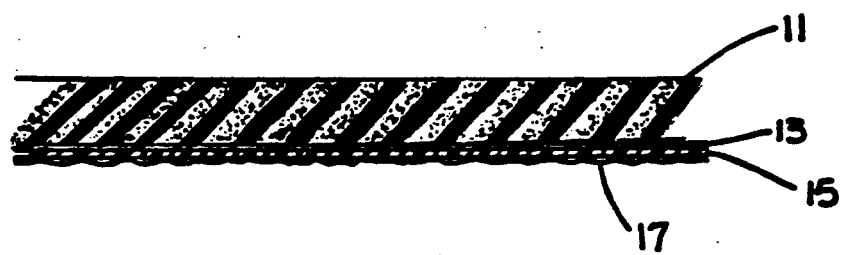
FIG. 4 describes an enlarged cross section of the inventive body protection material as shown previously by FIG. 1, with the addition of a coating of hydrophilic, liquid water impermeable, water vapor permeable polyurethane applied to the inner surface of the permeable polyurethane applied to the inner surface of the layer of porous expanded PTFE intended to be in contact with the skin of a wearer.

FIG. 4 shows an enlarged cross section of the inventive material made as shown previously by FIG. 1, except that the layer of porous expanded PTFE 15 has a coating of hydrophilic, liquid water impermeable, water vapor permeable polyurethane 17 on the inner surface so as to be in contact with the skin of a wearer. While this coating 17 is shown to be on the surface of the porous expanded PTFE 15, typically the coating 17 penetrates and fills the pores of the porous expanded PTFE 15 closest to the surface. The result is that the thickness of the layer of porous expanded PTFE 15 is increased almost imperceptably in amounts such as about 0.0001 inches.

Figure 5:
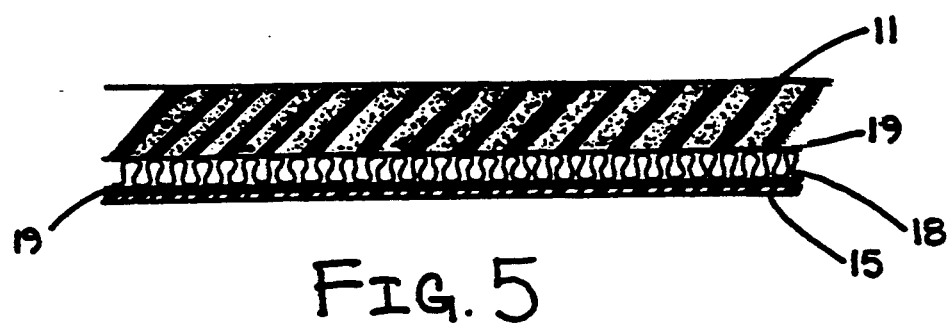
FIG. 5 shows an alternative embodiment incorporating a thin layer of air permeable padding between the outer layer of cellular rubber and the inner layer of porous expanded PTFE.

FIG. 5 describes an alternative embodiment having an additional thin layer of air permeable padding 18 applied between the outer layer of cellular rubber 11 and the inner layer of porous expanded PTFE 15. The presence of the padding increases the ability of the inventive body protection material to absorb perspiration. Suitable padding materials include open cell foam rubbers; preferred thicknesses are about 0.060 inches to about 0.100 inches. The layer of air permeable padding 18 is adhered to the adjacent layers of cellular rubber 11 and porous expanded PTFE 15 with layers of adhesive 19 which may be of the same types of adhesives described previously, applied either continuously or discontinuously.

EXAMPLE 1

A Stromgren Model 864 knee brace (Hays, KS), made of about 0.200 inch thick cellular neoprene rubber and having a supporting layer of fabric bonded to its outer surface, was turned inside out to allow its inner surface to be laminated to a film of porous expanded PTFE. A film of porous expanded PTFE was manufactured according to the teachings of U.S. Pat. Nos. 3,953,566 and 4,187,390. The finished film had a thickness of about 0.0015 inches, a porosity of 80%, a mass/unit area of 17 g/m$^2$, an inverted cup moisture vapor transmission rate of 24,000 g/m$^2$/hr (according to ASTM E96), a Teledyne Gurley value of 11 seconds (according to Federal Test Method Std. No. 191A), and a maximum pore size range of 0.2–2.0 microns determined by a methanol bubble point test (according to ASTM F316-86).

A sheet of film was cut to a size larger than the inner surface of the knee brace. One surface of the film was sprayed with Bostik SuperTak ™ Adhesive number 150724 (Middleton, Mass.). The inner surface of the inverted knee brace was placed into contact with one edge of the adhesive coated film surface and rolled across the film surface under hand pressure, causing the sheet of film to adhere to the inner surface of the knee brace. The adhesive was then allowed to air dry at room temperatures for one hour. The excess film was then trimmed from the edges of the knee brace, after which the knee brace was again inverted so that the film covered surface was on the inside of the knee brace. The laminated knee brace was then worn on one knee by a human test subject during one hour of basketball and an immediate subsequent hour of rest while a standard Stromgren model 864 knee brace was worn on the other knee for comparison. The laminated knee brace was found to be easier to put on than the control and much easier to remove. Further, the laminated knee brace was found to be much more comfortable; the standard brace began to cause itching when sweat formed under the brace after about ten minutes of wear while the laminated brace remained comfortable for the duration of the two hour test.

EXAMPLE 2

A second Stromgren Model 864 knee brace was laminated to a layer of porous expanded PTFE in a similar fashion as the previous example. The same film material of porous expanded PTFE was used, except that one surface of the porous expanded PTFE film was given a non-porous coating of hydrophilic, liquid water impermeable, water vapor permeable polyurethane as taught by U.S. Pat. No. 4,194,041. This coated film had a thickness of about 0.0015 inches, a mass/unit area of 28 g/m$^2$. The coated film demonstrated an inverted cup moisture vapor transmission rate of 19,800 g/m$^2$/hr. The film was given a discontinuous coating of Bostik Supertak Adhesive No. 150724, applied by spraying in a dot-matrix pattern of circular spots of about 0.5 inch diameter located about 2 inches apart on center. The adhesive was applied only to the surface of the porous expanded PTFE film that was not coated with polyurethane. This adhesive coated surface was adhered to the inner surface of the knee brace in the same manner as described for Example 1. The resulting laminated knee brace having an inner layer of porous expanded PTFE with a coating of polyurethane against the skin of the wearer was worn on one knee of a test subject in comparison to a standard Stromgren Model 864 knee brace worn on the other knee. The comparison was made during a wear period of one hour of bicycling followed by one hour of rest. The laminated knee brace was found to be comfortable for the two hour test period and further was found to be easy to put on and remove. The standard knee brace began to cause itching after sweat began to form between the knee brace and the covered skin surface after about 10 minutes of bicycling. The standard knee brace was also more difficult to put on and considerably more difficult to remove.

EXAMPLE 3

A sheet of the polyurethane coated porous expanded PTFE film used for Example 2 was laminated to a padding of 0.100 inch thick open cell air permeable foam rubber from Foamex Company (Eddystone, Pa., Part No. 275D) using the same Bostik adhesive described previously, applied in a continuous fashion to the surface of the porous expanded PTFE film. The adhesive was applied to the uncoated surface of the polyurethane coated porous expanded PTFE film, so that the polyurethane coated surface was away from the surface of the foam rubber to which the film was adhered. The surface of the foam rubber opposite the film covered surface was then sprayed with a thin coating of the same adhesive and adhered to the inner surface of a model 864 Stromgren knee brace in the same fashion as described previously for Examples 1 and 2. The finished laminated knee brace comprised, in sequence from the outer surface to the inner surface, a layer of substantially air impermeable cellular neoprene rubber, a layer of air permeable, open cell foam rubber, and a layer of porous expanded PTFE film having a polyurethane coating on the inner skin-contacting surface. The completed laminated knee brace was worn by a test subject in comparison to a standard Stromgren Model 864 knee brace for a one hour period of basketball followed by a one hour period of rest. The result of the comparison was the same result found for the comparison of Example 1, except that the laminated knee brace of Example 3 seemed subjectively to absorb more perspiration than did the laminated knee brace of Example 1 worn in an earlier test by the same test subject. No subjective improvement in comfort was noted over the laminated knee brace of Example 1.

EXAMPLE 4

A two inch square sample of porous expanded PTFE film of the type used to make Example 1 was bonded to the inner surface of a knee brace of the same type used for the previous examples, using a thin layer of Dow Corning Silastic Type A Medical Adhesive (part no. 891; Midland, Mich.). This silicone adhesive was allowed to air dry for 48 hours. After this drying period, it was found by attempting to pull the porous expanded PTFE film free from the knee brace that the silicone adhesive had produced a superior bond to that of the Bostik adhesive used for the previous examples. The silicone adhesive is considered to be a preferred adhesive for the present invention because of its superior bonding capability and because it is approved for medical device applications.

I claim:

1. A body protection material consisting essentially of a laminate of:
   a) an outer layer of substantially air impermeable cellular rubber; and b) an inner layer of porous expanded polytetrafluoroethylene wherein the inner layer is bonded directly to the outer layer with an adhesive selected from the group consisting of silicone adhesives, polyurethane adhesives, acrylic adhesives and rubber-based adhesives.

2. A body protection material according to claim 1 wherein the inner layer of porous expanded polytetrafluoroethylene has a coating of hydrophilic liquid water impermeable and water vapor permeable polyurethane.

3. A body protection material according to claim 2 wherein the coating is on the side of the inner layer of porous expanded polytetrafluoroethylene that is opposite the outer layer of cellular rubber.

4. A body protection material according to claim wherein the coating is between the outer layer of cellular rubber and the inner layer of porous expanded polytetrafluoroethylene and serves as the adhesive between the outer layer and the inner layer.

5. A body protection material according to claim 1 wherein a layer of fabric is laminated to the surface of the outer layer of substantially air impermeable cellular rubber opposite the inner layer of porous expanded polytetrafluoroethylene.

6. A body protection material according to claim 4 wherein a layer of fabric is laminated to the surface of the outer layer of substantially air impermeable cellular rubber opposite the inner layer of porous expanded polytetrafluoroethylene.

* * * * *